(12) United States Patent
De Felice et al.

(10) Patent No.: US 7,292,883 B2
(45) Date of Patent: Nov. 6, 2007

(54) PHYSIOLOGICAL ASSESSMENT SYSTEM

(75) Inventors: Claudio De Felice, Sienna (IT); Mitchell Goldstein, Northridge, CA (US); Giuseppe Latini, Brindis (IT)

(73) Assignee: Masimo Corporation, Irvine, CA (US)

( * ) Notice: Subject to any disclaimer, the term of this patent is extended or adjusted under 35 U.S.C. 154(b) by 133 days.

(21) Appl. No.: 11/094,813

(22) Filed: Mar. 30, 2005

(65) Prior Publication Data

US 2006/0009687 A1    Jan. 12, 2006

Related U.S. Application Data

(60) Provisional application No. 60/558,426, filed on Mar. 31, 2004.

(51) Int. Cl.
*A61B 5/00* (2006.01)

(52) U.S. Cl. ..................................... 600/324

(58) Field of Classification Search ................ 600/323, 600/300, 310, 324, 500; 702/19
See application file for complete search history.

(56) References Cited

U.S. PATENT DOCUMENTS

| | | |
|---|---|---|
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,337,744 A | 8/1994 | Branigan |
| 5,431,170 A | 7/1995 | Mathews |
| 5,452,717 A | 9/1995 | Branigan et al. |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,590,649 A | 1/1997 | Caro et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |

(Continued)

FOREIGN PATENT DOCUMENTS

EP    0 807 402 A1    11/1997

OTHER PUBLICATIONS

De Felice et al., "The pulse oximeter perfusion index as a predictor for high illness severity in neonates", European Journal of Pediatrics, pp. 561-562, 2002.*

(Continued)

*Primary Examiner*—Eric F Winakur
(74) *Attorney, Agent, or Firm*—Knobbe, Martens, Olson & Bear, LLP

(57) ABSTRACT

A physiological assessment system comprises a sensor and first and second processors. The sensor is adapted to generate a signal responsive to a living organism. The first processor is configured to derive a measured parameter from the sensor signal. The second processor is configured to analyze nonlinear dynamics of the measured parameter so as to provide a physiological assessment of the living organism.

17 Claims, 3 Drawing Sheets

U.S. PATENT DOCUMENTS

| | | | |
|---|---|---|---|
| 5,766,127 A * | 6/1998 | Pologe et al. ............... 600/310 |
| 5,769,084 A | 6/1998 | Katz et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,862,805 A * | 1/1999 | Nitzan ......................... 600/479 |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,236,872 B1 | 5/2001 | Diab et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,334,065 B1 | 12/2001 | Al-Ali et al. |
| 6,349,228 B1 | 2/2002 | Kiani et al. |
| 6,360,114 B1 | 3/2002 | Diab et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,515,273 B2 | 2/2003 | Al-Ali |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Diab et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,725,075 B2 | 4/2004 | Al-Ali |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,856,831 B2 | 2/2005 | Griffin et al. |
| 6,861,639 B2 | 3/2005 | Al-Ali |
| 6,939,307 B1 * | 9/2005 | Dunlop ..................... 600/504 |
| 6,990,426 B2 * | 1/2006 | Yoon et al. ................. 702/139 |
| 7,194,300 B2 * | 3/2007 | Korzinov .................... 600/518 |
| 2003/0181798 A1 | 9/2003 | Al-Ali |

OTHER PUBLICATIONS

Patent Abstract of Japan; Publication No. 11009557; Publication Date: Jan. 19, 1999.

Caceres, J.L.H. et al., "*The Photoplethismographic Signal Processed with Nonlinear Time Series Analysis Tools*", Revista Cubana de Informatica Medica, No. 1, pp. 1-10 (2000).

http://www.physionet.org/tutorials/ndc/ : Nonlinear Dynamics, Fractals, and Chaos Theory: Implications for Neuroautomatic Heart Rate Control in Health and Disease by Ary L. Goldberger, 1999.

* cited by examiner

PHYSIOLOGICAL ASSESSMENT SYSTEM

CROSS-REFERENCE TO RELATED APPLICATIONS

This application relates to and claims the benefit of prior U.S. Provisional Application No. 60/558,426 entitled Chaotic Analysis of Pulse Oximetry Signals in the Assessment of Neonatal Illness Severity, filed Mar. 31, 2004 and incorporated by reference herein.

BACKGROUND OF THE INVENTION

Pulse oximetry is a noninvasive, easy to use, inexpensive procedure for measuring the oxygen saturation level of arterial blood. Pulse oximeters perform a spectral analysis of the pulsatile component of arterial blood in order to determine the relative concentration of oxygenated hemoglobin, the major oxygen carrying constituent of blood. By providing early detection of decreases in the arterial oxygen supply, pulse oximetry reduces the risk of accidental death and injury. As a result, pulse oximeters have gained rapid acceptance in a wide variety of medical applications, including surgical wards, intensive care units, general wards and home care.

A typical pulse oximeter comprises a sensor and a monitor. The sensor has emitters and a detector and is attached to a patient at a selected tissue site, such as a fingertip or ear lobe. The emitters project light at red and infrared (IR) wavelengths through the blood vessels and capillaries of the tissue site. The detector is positioned so as to detect the emitted light as it emerges from the tissue site. The signal generated by the detector is proportional to the intensity of the detected light. The detector signal has a variable (AC) component due to light absorption by the pulsatile volume of arterial blood. The detector signal also has a constant (DC) component due to light absorption by the non-pulsatile volume of arterial blood, venous blood, bone and other tissue. A signal processor inputs the detector signal and determines oxygen saturation and pulse rate, which are typically shown as a numerical readout on a display. In addition to oxygen saturation and pulse rate (PR), some pulse oximeters measure perfusion index (PI), which is a relative indication of pulse strength at a monitoring site. In particular, PI is the ratio of the IR AC signal to the IR DC signal. A pulse oximetry sensor and monitor are described, respectively, in U.S. Pat. No. 6,088,607 entitled Low Noise Optical Probe and U.S. Pat. No. 5,482,036 entitled Signal Processing Apparatus and Method, both of which are assigned to Masimo Corporation, Irvine, Calif. and incorporated by reference herein.

SUMMARY OF THE INVENTION

Nonlinear dynamics is the study of systems governed by equations in which a small change in one variable can induce a large systematic change. Chaos theory is one aspect of nonlinear dynamics, which attempts to construct deterministic, nonlinear dynamic models that elucidate irregular, unpredictable behavior. Chaos theory teaches that complex non-linear systems may not reach steady state, but will behave chaotically depending on minute changes in environmental conditions. Nonlinear dynamics can be advantageously applied to analyze the variability of physiological parameters for illness assessment. For example, chaos data analysis is applied to real-time pulse oximetry signals, including perfusion index or pulse rate or both, so as to determine or predict the severity of patient illness or, in contrast, the degree of patient wellness.

A healthy individual has a physiological system with a complex dynamic that enables it to adapt to a constantly changing environment. Many serious diseases have pathologies that reduce the dynamic complexity of the human physiological system. This translates into reduced variability of measurable physiological parameters, such as those derived by pulse oximetry. As such, the variability of measured physiological parameters can be used to assess illness severity. Use of non-invasively-obtained physiological parameters, for example, parameters obtained through the use of pulse-oximetry, has the advantage that system variability may be monitored continuously and the onset of serious disease may therefore be detected sooner than would otherwise be possible. The early detection of serious disease can be especially important with patients that are highly susceptible and for whom the time interval between disease onset and mortality can be very short, such as neonatal patients.

One aspect of a physiological assessment system is a sensor and first processor and a second processor. The sensor is adapted to generate a signal responsive to a living organism. The first processor is configured to derive a measured parameter from the sensor signal. The second processor is configured to analyze nonlinear dynamics of the measured parameter so as to provide a physiological assessment of the living organism. In one embodiment, the sensor is adapted to transmit optical radiation of at least two wavelengths into a tissue site and generate a detector signal responsive to the optical radiation after absorption by pulsatile blood flow within the tissue site, the first processor is a pulse oximeter and the measured parameter is a perfusion index. The second processor may calculate a statistic responsive to the variability of the perfusion index and the physiological assessment may correspond to illness severity. Further, the statistic may be determined by chaos data analysis, which may be compared to a predetermined normality range. In a particular embodiment, the pulse oximeter derives a second measured parameter and the second processor calculates a second statistic responsive to the variability of the second measured parameter, wherein the second measured parameter may be pulse rate.

Another aspect of a physiological assessment system is a pulse oximeter, a variability analyzer and a statistics interpreter. The pulse oximeter is adapted to measure a perfusion index. The variability analyzer is configured to provide a statistic or statistics responsive to variability of the perfusion index. The statistics interpreter is configured to indicate illness severity based upon the statistic or statistics. The physiological assessment system may further comprise a data storage for compiling time series data for the perfusion index. The system may also comprise a visual indication of perfusion index variability or illness severity or both. In addition, the system may comprise an aural indication of perfusion index variability or illness severity or both. In one embodiment, the analyzer is a chaos data analyzer. A predetermined range may be input to the interpreter, wherein the interpreter is capable of comparing a statistic or statistics to the range so as to indicate illness severity.

A further aspect of a physiological assessment system comprises time series data derived for at least one physiological parameter and a nonlinear dynamics measure calculated based upon the time series data. The nonlinear dynamics measure is evaluated with respect to a predetermined criterion, and a physiological assessment is provided based upon the evaluation. The time series data may be a perfusion index measured with a pulse oximeter. The nonlinear dynamics measure may be a variability measure obtained for the perfusion index. The variability measure may be compared to a predetermined cutoff value, and an illness severity indication may be outputted. In a particular embodiment, a pulse rate is also measured and a variability measure is calculated for the combination of perfusion index and pulse rate. A chaos data analysis may be performed on the time series data.

DETAILED DESCRIPTION OF THE PREFERRED EMBODIMENTS

Figure 1:
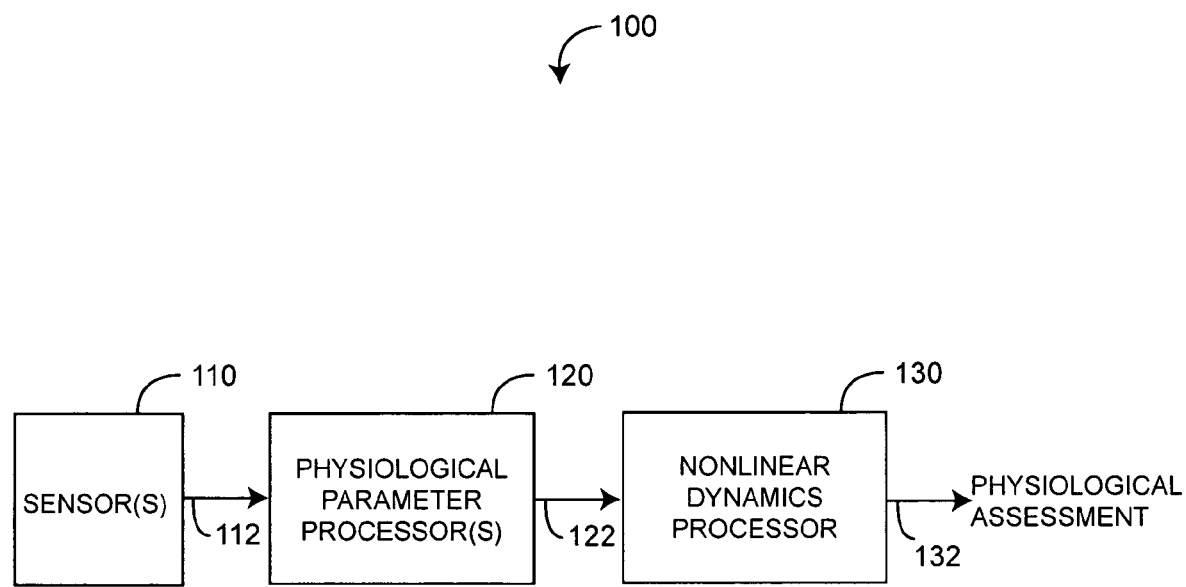
FIG. 1 is a general block diagram of a physiological assessment system.

FIG. 1 illustrates a physiological assessment system 100 that advantageously monitors the nonlinear dynamics of one or more physiological parameters 122 so as to provide a physiological assessment 132 of a living organism. The physiological assessment system 100 has one or more sensors 110 capable of responding to a living organism so as to provide sensor signals 112 to one or more physiological parameter processors 120. The physiological parameter processors 120 provide measured parameters 122 derived from the sensor signals 112. A nonlinear dynamics processor 130 analyzes the dynamics of the measured parameters 122 so as to provide a physiological assessment 132 of the living organism. A sensor(s) 110 may be a pulse oximetry sensor, a blood pressure transducer, ECG or EEG electrodes or a capnometer, or a combination of these, to name a few. The physiological parameter processor(s) 120, accordingly, may be a pulse oximeter, a blood pressure monitor, an ECG monitor, an EEG monitor, a $CO_2$ monitor or a multi-parameter patient monitor, or a combination of these, to name a few. Likewise, the measured parameters 122 may be, as examples, oxygen saturation, pulse rate, perfusion index, blood glucose, blood pressure and ETCO2 among others. The nonlinear dynamics processor 130 can be hardware, software or a combination that analyzes, for example, the variability of the measured parameters 122. The physiological assessment 132 may be a numerical readout, message or other visual display or an alarm or other audible indication, or a combination of these. The physiological assessment 132 may assist in the determination of illness severity, wellness, or depth of sedation, to name a few; may provide information helpful for triage in emergency, hospital or surgical environments, for example; or may help in the prediction of, for instance, recovery time, length of hospitalization or medical costs.

Figure 2:
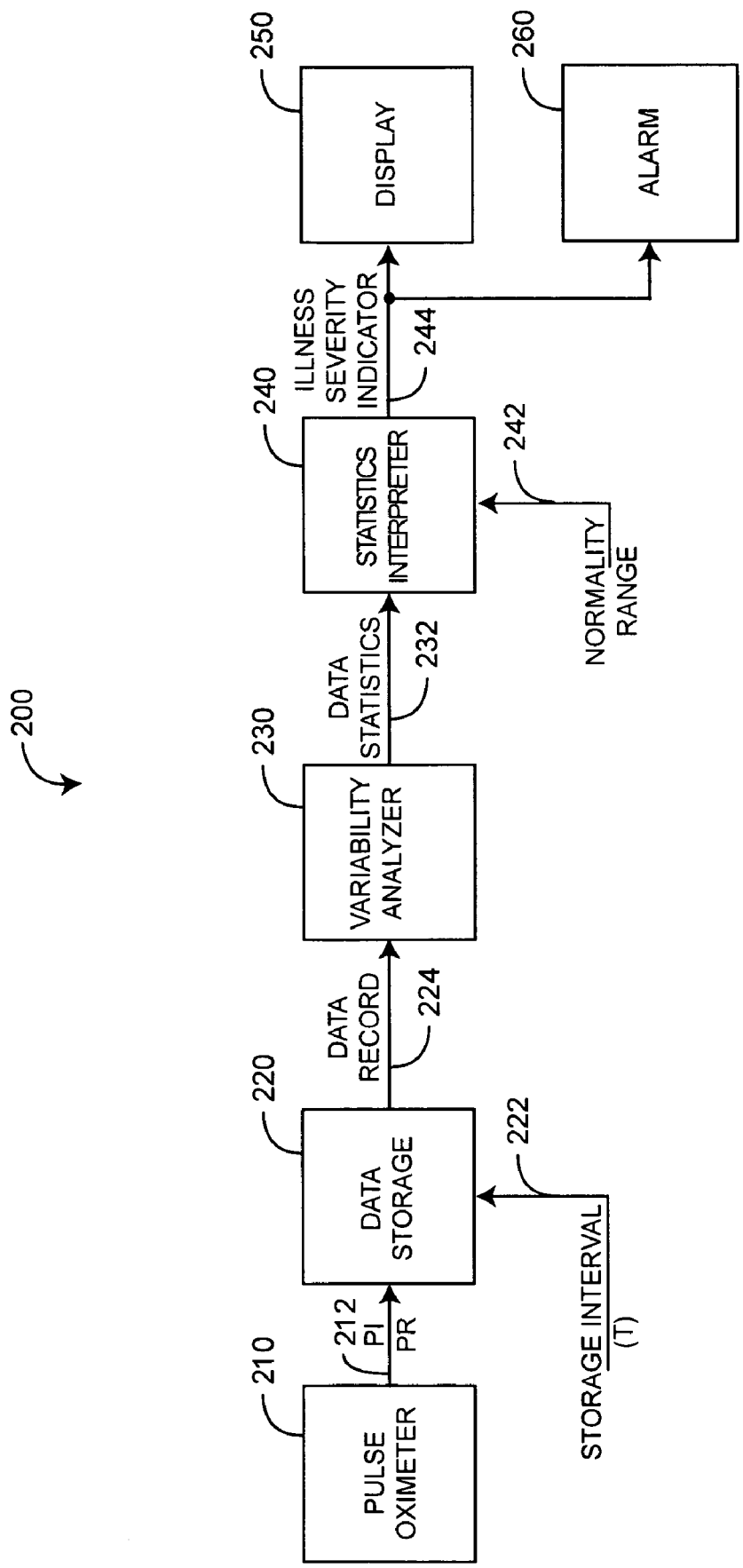
FIG. 2 is a block diagram of one embodiment of a physiological assessment system.

FIG. 2 illustrates one embodiment of a physiological assessment system 200 having a pulse oximeter 210, a data storage 220, a variability analyzer 230 and a statistics interpreter 240. The pulse oximeter 210 measures parameters 212 such as perfusion index (PI) or pulse rate (PR) or a combination of PI and PR. The data storage 220 compiles a trend of the parameters 212 so as to create a data record 224. The data record length (T) is set by a predetermined storage interval input 222. The variability analyzer 230 processes the data record 224 so as to provide data statistics 232. In a particular embodiment, the variability analyzer 230 is a Chaos Data Analyzer (CDA-Pro) available from The Academic Software Library, North Carolina State University, Raleigh, N.C. The CDA-Pro performs various tests for detecting hidden determinism in a seemingly random time series, such as the probability distribution, power spectrum, Lyapunov exponent, and various measures of the fractal dimension. The statistics interpreter 240 evaluates the data statistics 232 to determine if variability is in a normal or abnormal range and provides an illness severity indicator 244 accordingly. A predetermined normality range input 242 sets this range. The illness severity indicator 244 may be displayed 250 or may trigger an alarm 260 or both. In an alternative embodiment, the range input 242 may specify multiple ranges, which may include one or more of variability above a normal level indicating illness, variability within a normal range, variability within an indeterminate range, and variability below a normal range indicating illness. The range input 242 may also be a threshold or cutoff between normal and abnormal variability. In another embodiment, PR variability may be used as an early predictor of a return to health, and PI variability may be used as an early predictor of the onset of illness.

In a particular embodiment, the pulse oximeter 210 incorporates the data storage 220, variability analyzer 230 and statistics interpreter 240. The display 250 is a scaled readout on a pulse oximeter 210 showing PI variance on a relative scale having a gauge of maximum and minimum ranges. An alarm 260 is configured to sound when PI variance drops below a predetermined level.

Figure 3:
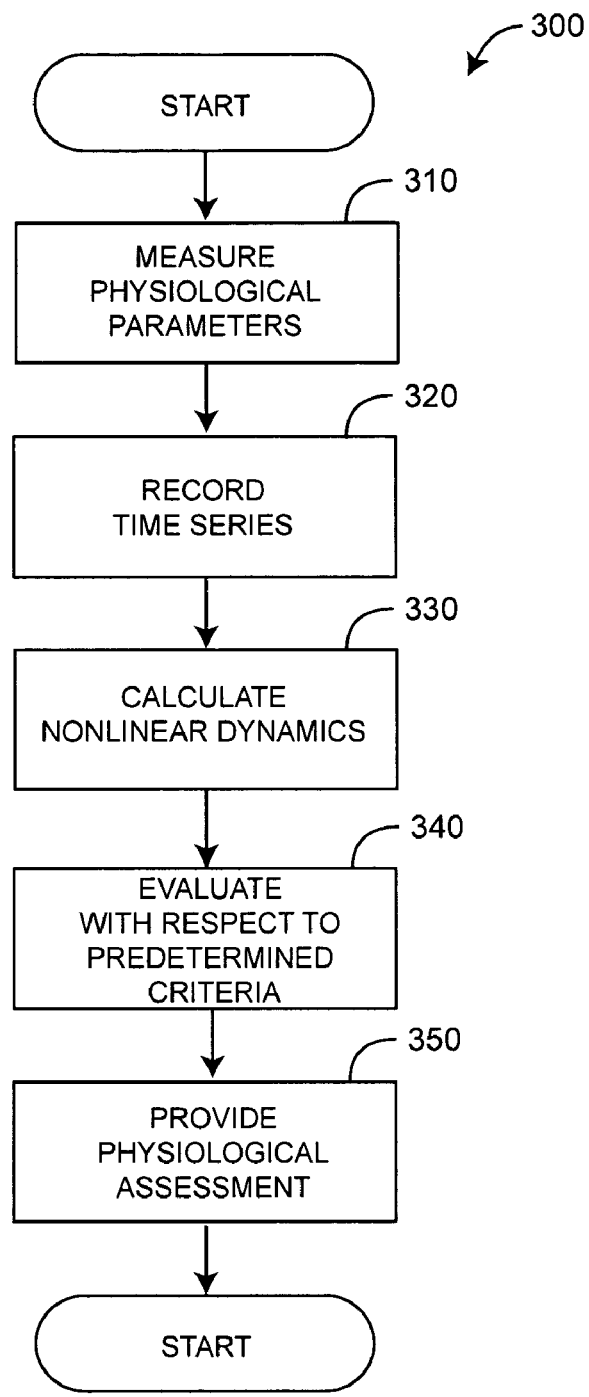
FIG. 3 is a flowchart of a physiological assessment process.

FIG. 3 illustrates a physiological assessment method 300 wherein physiological parameters are iteratively measured 310 and recorded as a time series 320. The physiological parameters may be, for example, perfusion index or pulse rate or both. Nonlinear dynamics of the time series are calculated 330. These calculations may be based upon chaos data analysis. The nonlinear dynamics are evaluated with respect to predetermined criteria 340 so as to provide a physiological assessment 350. In one embodiment, the nonlinear dynamics may provided a measure of variability of the physiological parameter or parameters, which may be compared to a range of normal or abnormal variability or, alternatively, a threshold or cutoff value or variability so as to assess illness severity or depth of sedation, for example.

A physiological assessment system has been disclosed in detail in connection with various embodiments. These embodiments are disclosed by way of examples only and are not to limit the scope of the claims that follow. One of ordinary skill in art will appreciate many variations and modifications.

What is claimed is:

1. A physiological assessment system comprising:
   a sensor adapted to transmit optical radiation of at least two wavelengths into a tissue site and generate a detector signal responsive to said optical radiation after absorption by pulsatile blood flow within said tissue site;
   a pulse oximeter configured to derive a perfusion index from said signal; and
   a second processor configured to analyze nonlinear dynamics of said perfusion index and to provide an illness severity indicator indicating at least a readily identifiable normal or abnormal state.

2. The physiological assessment system according to claim 1 wherein:
   said second processor calculates a statistic responsive to the variability of said perfusion index.

3. The physiological assessment system according to claim 2 wherein said statistic is determined by chaos data analysis.

4. The physiological assessment system according to claim 2 wherein said statistic is compared to a predetermined normality range.

5. The physiological assessment system according to claim 2 wherein:
said pulse oximeter derives a second measured parameter, and
said second processor calculates a second statistic responsive to the variability of said second measured parameter.

6. The physiological assessment system according to claim 5 wherein said second measured parameter is pulse rate.

7. A physiological assessment system comprising:
a pulse oximeter adapted to measure a perfusion index;
an analyzer configured to provide at least one statistic responsive to variability of said perfusion index; and
an interpreter configured to indicate illness severity based upon said at least one statistic.

8. The physiological assessment system according to claim 7 further comprising a data storage for compiling time series data for said perfusion index.

9. The physiological assessment system according to claim 7 further comprising a visual indication of at least one of perfusion index variability and illness severity.

10. The physiological assessment system according to claim 7 further comprising an aural indication of at least one of perfusion index variability and illness severity.

11. The physiological assessment system according to claim 7 wherein said analyzer is a chaos data analyzer.

12. The physiological assessment system according to claim 7 further comprising:
a predetermined range input to said interpreter,
said interpreter capable of comparing said at least one statistic to said range so as to indicate illness severity.

13. A physiological assessment method comprising the steps of:
deriving time series data for at least one physiological parameter comprising the substep of measuring perfusion index with a pulse oximeter;
calculating a nonlinear dynamics measure based upon said time series data;
evaluating said nonlinear dynamics measure with respect to a predetermined criterion; and
providing an illness severity indicator indicating at least a readily identifiable normal or abnormal state based upon said evaluation.

14. The physiological assessment method according to claim 13 wherein said calculating step comprises the substep of obtaining a variability measure for said perfusion index.

15. A physiological assessment method according to claim 13 wherein said evaluating step comprises the substep of comparing said variability measure to a predetermined cutoff value.

16. The physiological assessment method according to claim 13 wherein:
said deriving step comprises the further substep of measuring pulse rate; and
said calculating step comprises the substep of obtaining a variability measure for the combination of said perfusion index and said pulse rate.

17. The physiological assessment method according to claim 13 wherein said evaluating step comprises the substep of performing a chaos data analysis on said time series data.

* * * * *

UNITED STATES PATENT AND TRADEMARK OFFICE
CERTIFICATE OF CORRECTION

PATENT NO. : 7,292,883 B2  Page 1 of 1
APPLICATION NO. : 11/094813
DATED : November 6, 2007
INVENTOR(S) : Claudio De Felice et al.

It is certified that error appears in the above-identified patent and that said Letters Patent is hereby corrected as shown below:

On sheet 3 of 3 (FIG. 3), below box 350, please delete "START" and insert -- END --, therefor.

At page 2, column 2 (Other Publications), line 3, please delete "Photoplethismographic" and insert -- Photoplethysmographic --, therefor.

At column 4, line 39, please delete "provided" and insert -- provide --, therefor.

At column 4, line 42, after "value", please delete "or" and insert -- of --, therefor.

Signed and Sealed this

Twelfth Day of August, 2008

JON W. DUDAS
*Director of the United States Patent and Trademark Office*